United States Patent
Lin

[19]

[11] Patent Number: 6,155,995

[45] Date of Patent: Dec. 5, 2000

[54] STRUCTURE OF A MULTIFUNCTIONAL EYE MASK

[76] Inventor: Pin-Hung Lin, P.O. Box 82-144, Taipei, Taiwan

[21] Appl. No.: 09/368,147

[22] Filed: Aug. 5, 1999

[51] Int. Cl.[7] .............................. A61H 1/00; A61H 7/00
[52] U.S. Cl. .............................. 601/15; 601/79; 601/148; 607/109
[58] Field of Search ................................... 601/15, 17, 18, 601/37, 70, 72, 79, 81, 132, 148–152; 607/100, 88, 109, 112, 108

[56] References Cited

U.S. PATENT DOCUMENTS

| | | | |
|---|---|---|---|
| 2,569,795 | 10/1951 | Avery | 601/151 |
| 2,690,173 | 9/1954 | Seeger et al. | 601/37 |
| 3,173,419 | 3/1965 | Dubilier et al. | 601/109 |
| 5,072,724 | 12/1991 | Marcus | 601/148 |
| 5,169,384 | 12/1992 | Bosniak | 607/108 X |
| 5,307,791 | 5/1994 | Senoue et al. | 601/9 |
| 5,336,159 | 8/1994 | Cheng | 601/15 |
| 5,569,166 | 10/1996 | Stone | 601/21 |
| 6,007,501 | 12/1999 | Cabados et al. | 601/134 X |
| 6,039,704 | 3/2000 | Domenighini | 601/79 |

Primary Examiner—Danton D. DeMille
Assistant Examiner—Denise Pothier
Attorney, Agent, or Firm—A & J

[57] ABSTRACT

An improved structure of a multifunctional eye mask comprising an elastic tightening strap, a main body, a heat healing device and a controller, characterized in that the elastic tightening strap is used to tie the mask to the eyes of user, the front section of the belt is mounted with the main body and the heat healing device, and the main body includes an air pump, an air releasing valve, a tube, a pair of vibration motors, a buzzer, a wiring board, and the exterior of the main body is provided with wires linked to the controller, the heat healing device consists of a front and a rear protective plate formed into a mask-like structure containing an air sac, a heat-emitting element, an air inlet for the air sac and the heat-emitting element are connected to the main body, the controller is provided with a circuit device with controlling switches and adjusting knobs on the surface thereof, thereby when in use, by means of the circuit device, the air sac and the heat emitting element expand and contract and emit heat respectively, and the sequence of action of the air sac and the heat emitting element are preset in the controller such that the eyes are provided with an intermittent massage, heat healing treatment and vibrating massage.

6 Claims, 8 Drawing Sheets

STRUCTURE OF A MULTIFUNCTIONAL EYE MASK

BACKGROUND OF THE INVENTION (a) Field of the Invention

The present invention relates to an improved structure of a multifunctional eye mask, and in particular, to a lightweight eye mask which provides a comfortable heat healing massage, intermittent massage and vibrating massage to the eyes of the wearer. The wearer can easy control the operation of the eye mask by means of the controller mounted to the eye mask.

(b) Description of the Prior Art

ROC Patent Publication No. 312156, entitled multifunctional heat healing and massaging device for eyes" employed electrical current to stimulate massaging of eyes can cause unsafe feeling to the user and may cause danger to the eyes. ROC Patent Publication No. 295859, entitled "eye sight adjusting device" employed air pressure to massage the eyes provides only a single function of massaging the eyes. ROC Patent Publication Nos. 109194 and 269186, entitled "massage device for eyes" and "electric fluid heat healing device for eyes" both employed liquid pressure to produce massaging action to the eyes. These devices can provide vibration massage and heat healing effects but they do not disclose a device having multiple functions such as expansion and contraction massage, vibration and heat healing. Besides, the devices disclosed in the prior art are of large size and complicated structure. Thus, it is not convenient to carry along.

SUMMARY OF THE INVENTION

Accordingly, it is an object of the present invention to provide an improved structure of a multifunctional eye mask, which is a small size and is easily operated.

Another object of the present invention is to provide an improved structure of a multifunctional eye mask, which provides simultaneous pneumatic massage, vibration massage, heat healing treatment to the eyes of the wearer.

An aspect of the present invention is to provide an improved structure of a multifunctional eye mask comprising an elastic tightening strap, a main body, a heat healing device and a controller, characterized in that the elastic tightening strap is used to tie the mask to the eyes of the user, the front section of the strap is mounted with the main body and the heat healing device, and the main body includes an air pump, an air releasing valve, a tube, a pair of vibration motors, a buzzer, a wiring board, and the exterior of the main body is provided with wires linked to the controller, the heat healing device consists of a front and a rear protective plate formed into a mask-like structure containing an air sac, a heat-emitting element, air inlet for the air sac and the heat-emitting element are connected to the main body; the controller is provided with a circuit device with controlling switches and adjusting knobs on the surface thereof, thereby when in use, by means of the circuit device, the air sac and the heat emitting element expand and contract and emit heats, and the sequence of action of the air sac and the heat emitting element are preset in the controller such that the eyes are provided with an intermittent massage, heat healing treatment and vibrating massage.

Reference is made to the attached drawings illustrating a preferred embodiment of the invention wherein.

DETAILED DESCRIPTION OF THE PREFERRED EMBODIMENT

Figure 8:
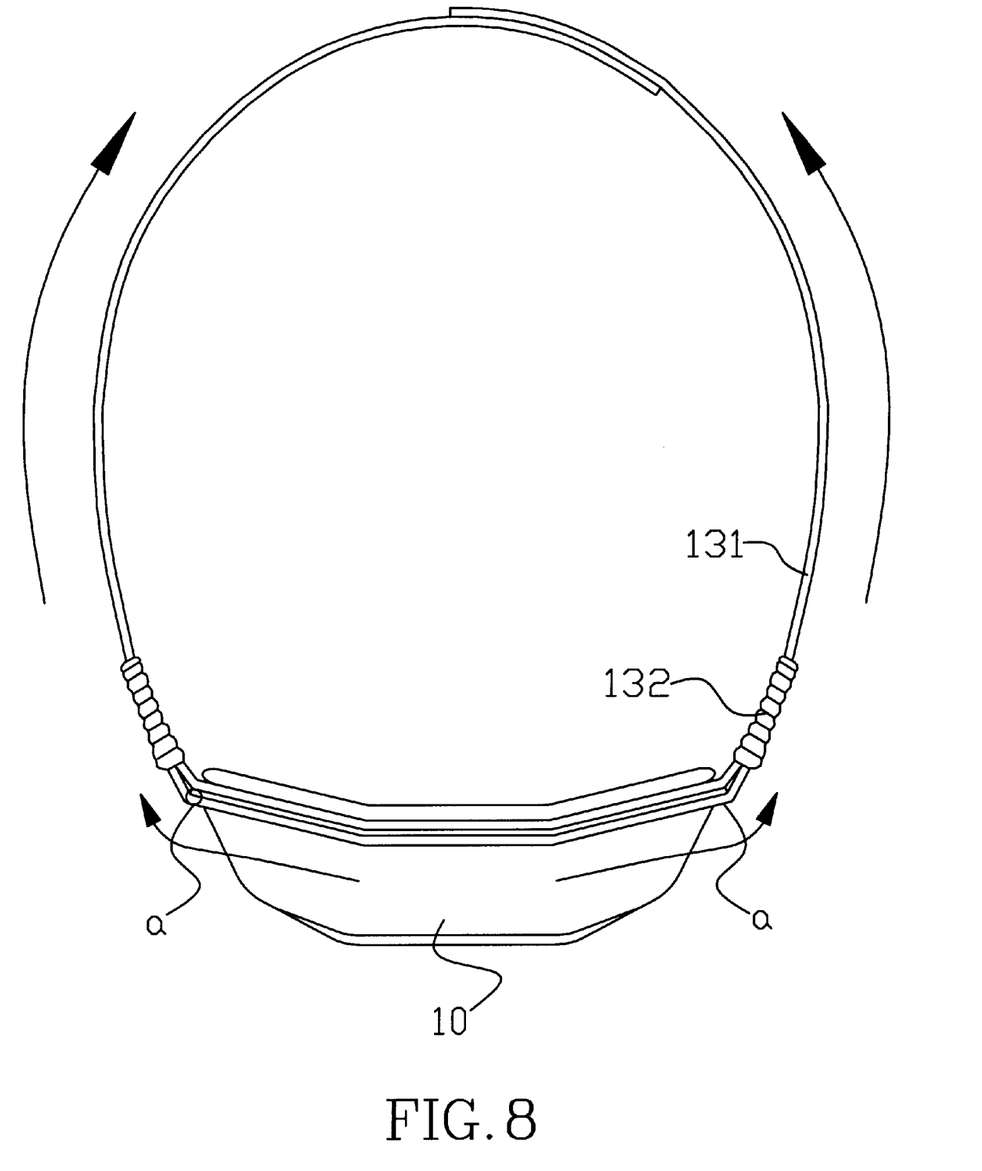
FIG. 8 is a top schematic view of the main body in combination with the elastic tightening strap of the eye mask of the present invention.

Referring to FIGS. 1, 2, 3 and 4, the eye mask of the present invention comprises a main body 10, a pneumatic heat healing device 20, and a controller 30, wherein the main body 10 consists of a front cover 11, and a rear cover 12. A protruded edge 121 on the rear cover 12 is used to combine with the front cover 11 together with a fixing plate 13. The two lateral sides of the fixing plate 13 are respectively extended to form an elastic tightening strap 131. As the strap 131 is elastic, the length of the strap 131 varies (as shown in FIG. 8) to mount onto the head of all wearers. A VELCRO fastener 133 is provided to the end section of the strap 131 for fastening. Within the main body 10, a wiring board 14, an air pump 15, an air-releasing valve 16, a tube 151, two vibration motors 17, and a buzzer 18 are contained. The air pump 15, the tube 151, and the valve 16 are in communication with each other. The tube 151 is extended slightly beyond an aperture 122 provided at the rear cover 12. The function of the air releasing valve 16 and the air pump 15 is to allow expansion and contraction of the pneumatic heat healing device 20. The vibration motors 17 are used to provide a vibrating effect, and the buzzer 18 is used to provide an indication of working status of the eye mask, such that the wearer, while the eyes are blocked, knows the current working status. The wiring board 14 is combined with all wires from the pertinent elements of the eye mask and is then linked to a wire 141 exposed on the surface of the main body 10 and then connected to the controller 30. An LED indicator 142 is also mounted to the wiring board 14 and is exposed on the surface of the main body 10 to indicate the working status.

Figure 3:
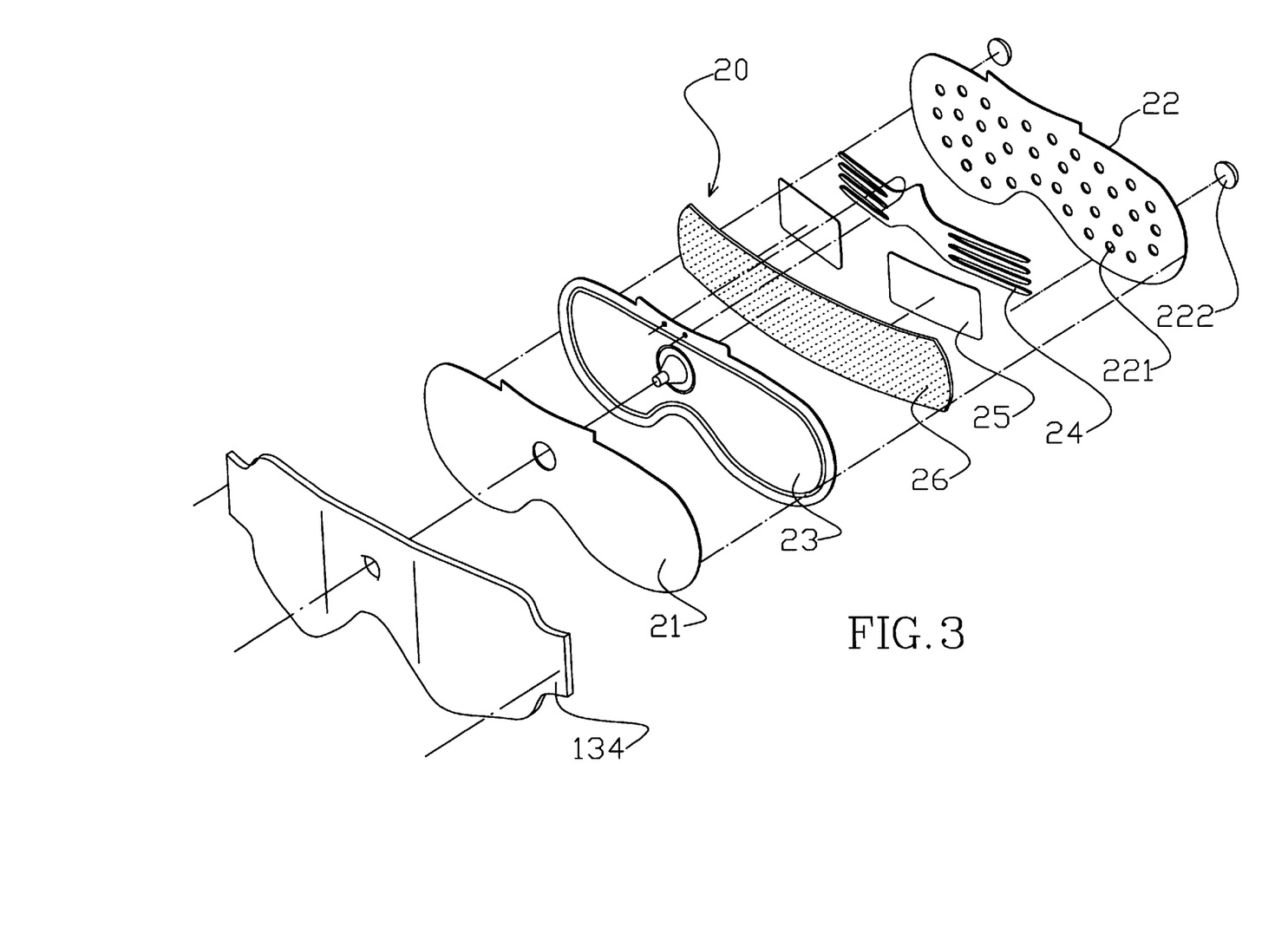
FIG. 3 is a perspective exploded view of the pneumatic heat healing device of the eye mask of the present invention.
Figure 4:
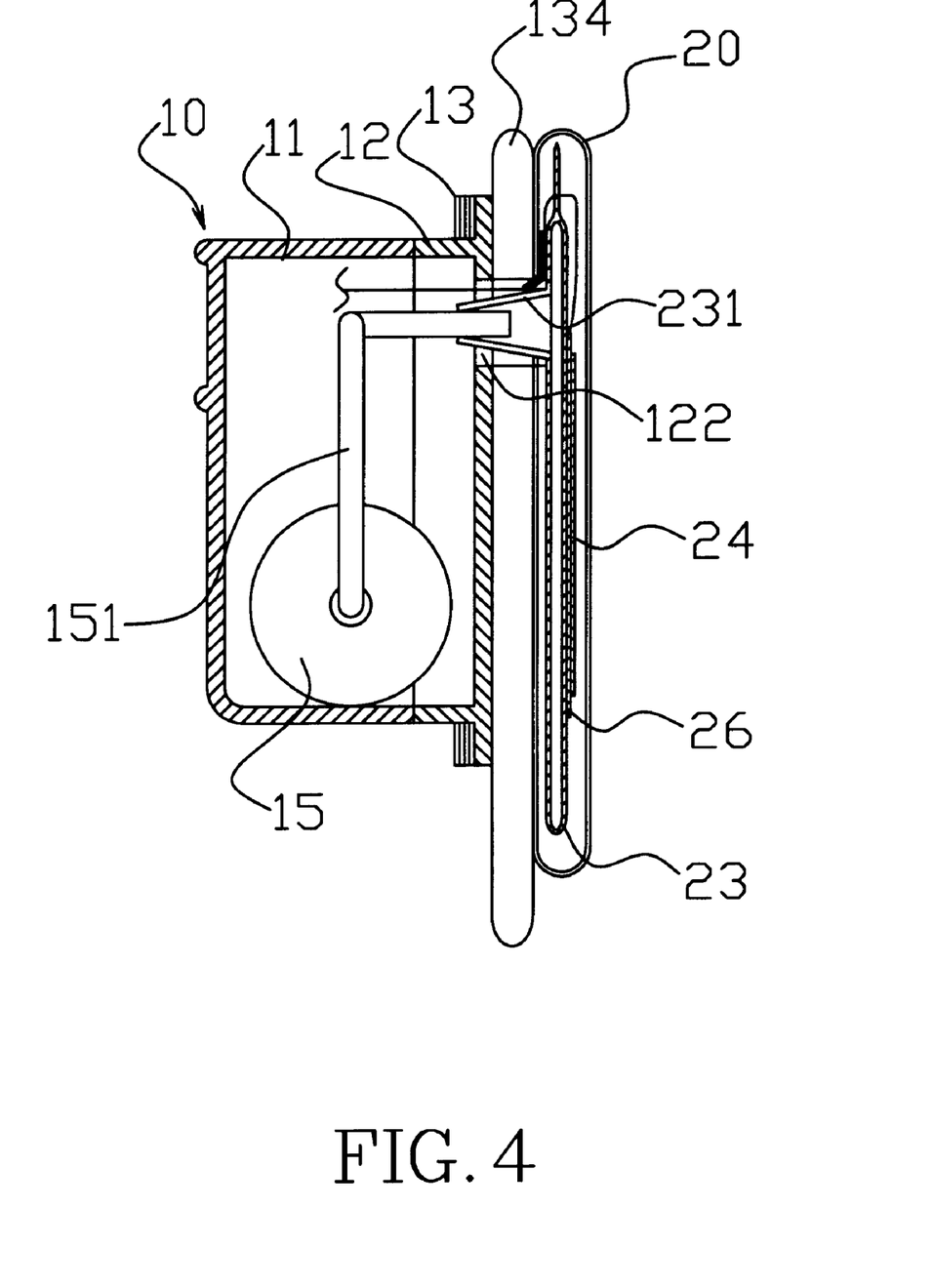
FIG. 4 is a sectional view of the eye mask of the present invention.

In accordance with the present invention, and as shown in FIG. 3, the pneumatic heat healing device 20 is located at the rear of the main body 1 and a liner 134 is mounted in between the main body 1 and the device 20. The lateral ends of the liner 134 are linked respectively to a retractable section 132 (refer to FIG. 1) of the tightening strap 131. The pneumatic heat healing device 20 consists of a front protective plate 21 and a rear protective plate 22 and the size of the plates 21, 22 is sufficient large to cover the eyes of the wearer. The external edge of the rear protective plate 22, i.e., the surface covering the eyes, is provided with a plurality of infra red protrusions 221 and magnetic stones 222, which are used to enhance blood circulation of the eyes. A sac 23, which is inflatable, is provided and is corresponding to the thin heat emitting element 24. The heat emitting element 24 is mounted to the heat insulation liner 26 by means of the adhesive plate 25, and the two lateral sides of the heat insulation liner 26 is mounted together with the front and rear protective plates 21, 22. This will effectively prevent the heat dissipation of heat energy from the heat emitting element 24, but, the heat energy of the element 24 is concentrated at the eyes to provide heat healing effect. The air inlet 231 at the top of the air sac 23 passes through the protective plate 21, the liner 134 and the rear cover 12 and extends into the main body 10 and connects with the tube 151. Thus, the main body 10 and the heat healing device 20 are combined together, and the main body 10 provides heat energy and air pressure to the heat healing device 20.

In accordance with the present invention, the controller 30 is provided with a circuit device (not shown) therein and a plurality of controlling switches and adjusting knobs on the surface thereof so as to facilitate pneumatic massage, vibration massage and to control the strength of all the massage action, and the temperature of heat healing treatment. The controller 30 also provides a selection of automatic massage sequences.

Figure 1:
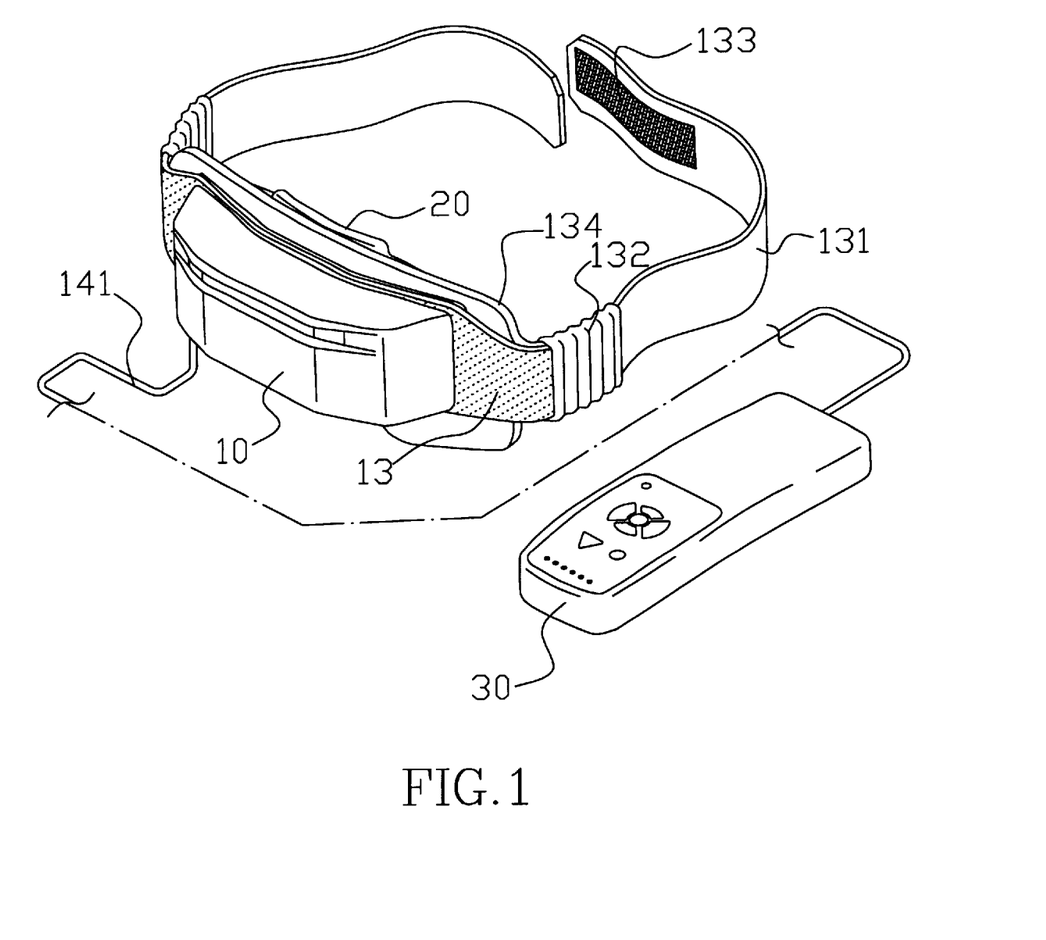
FIG. 1 is a perspective view of the present invention.
Figure 2:
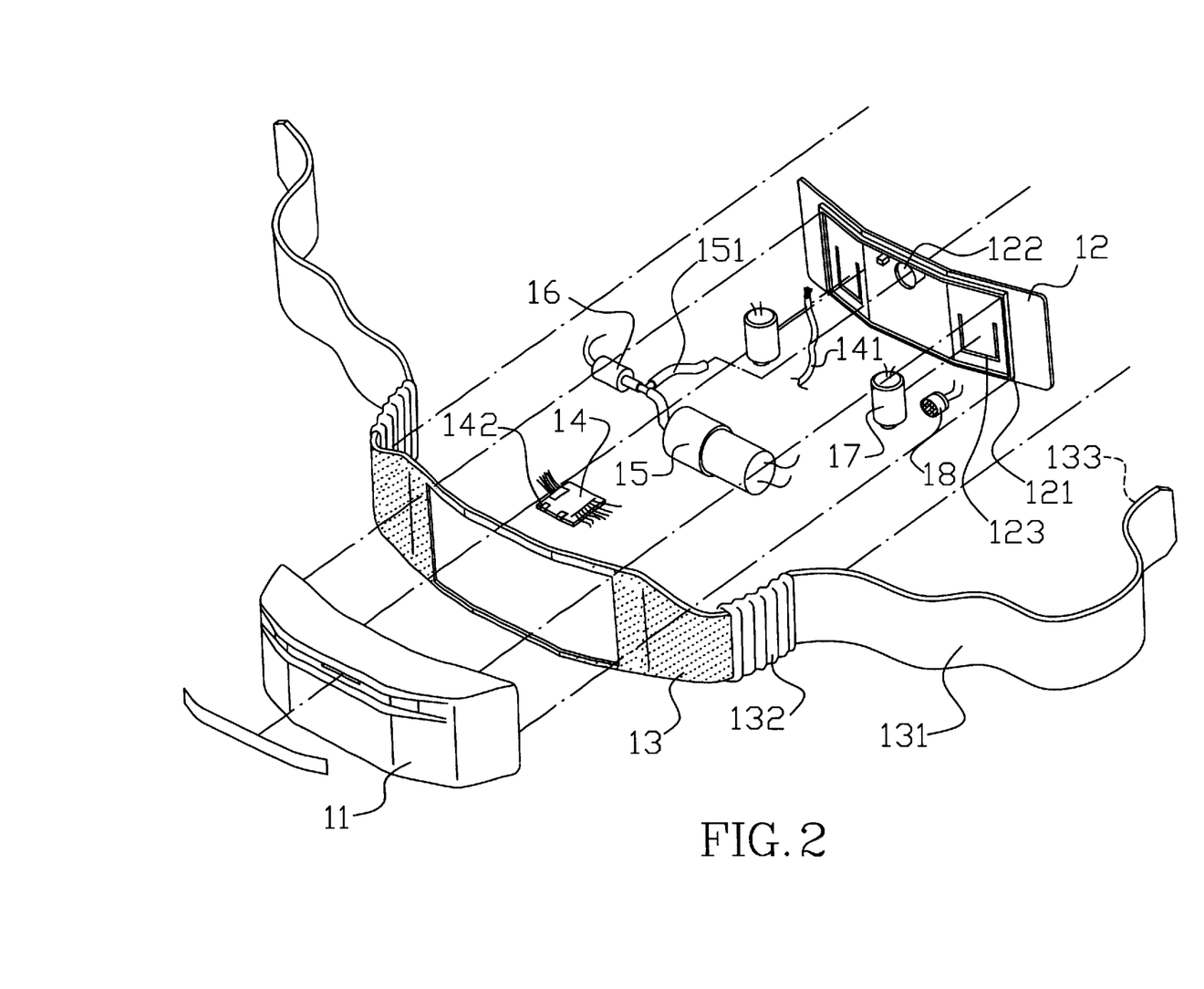
FIG. 2 is a perspective exploded view of the main body of the eye mask of the present invention.
Figure 5:
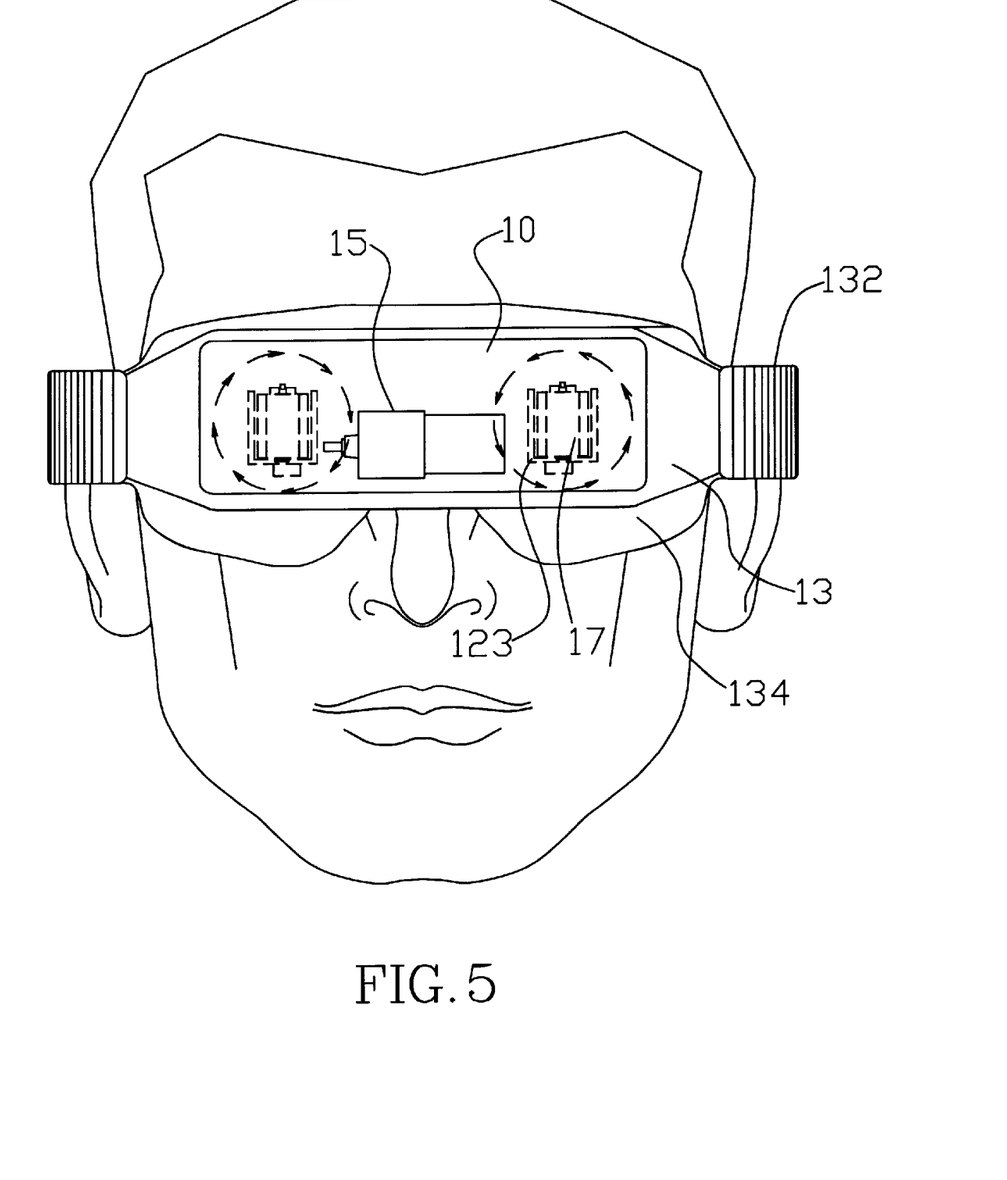
FIG. 5 is a schematic view illustrating pneumatic massage and heat healing treatment of the eye mask of the present invention.

Referring to FIGS. 1 and 5, the eye mask can be mounted onto the eyes of the wearer by the use of the tightening strap 131 and the controller 30 is used to control the strength of massage and the temperature of the heat healing treatment. All these conditions can be preset into the controller 30. By means of the circuit device, the air sac 23 provides an expansion and contraction force, and the heat emitting element 24 provides the heat energy for massaging and heat healing the eyes. In accordance with the present invention, the air sac 23 is retractable intermittently to provide an effect as that of massaging the eyes with the hands. The heat-emitting element 24 is provided with a safety temperature range. Thus, the heat-healing massage process is comfortable and safe.

Figure 6:
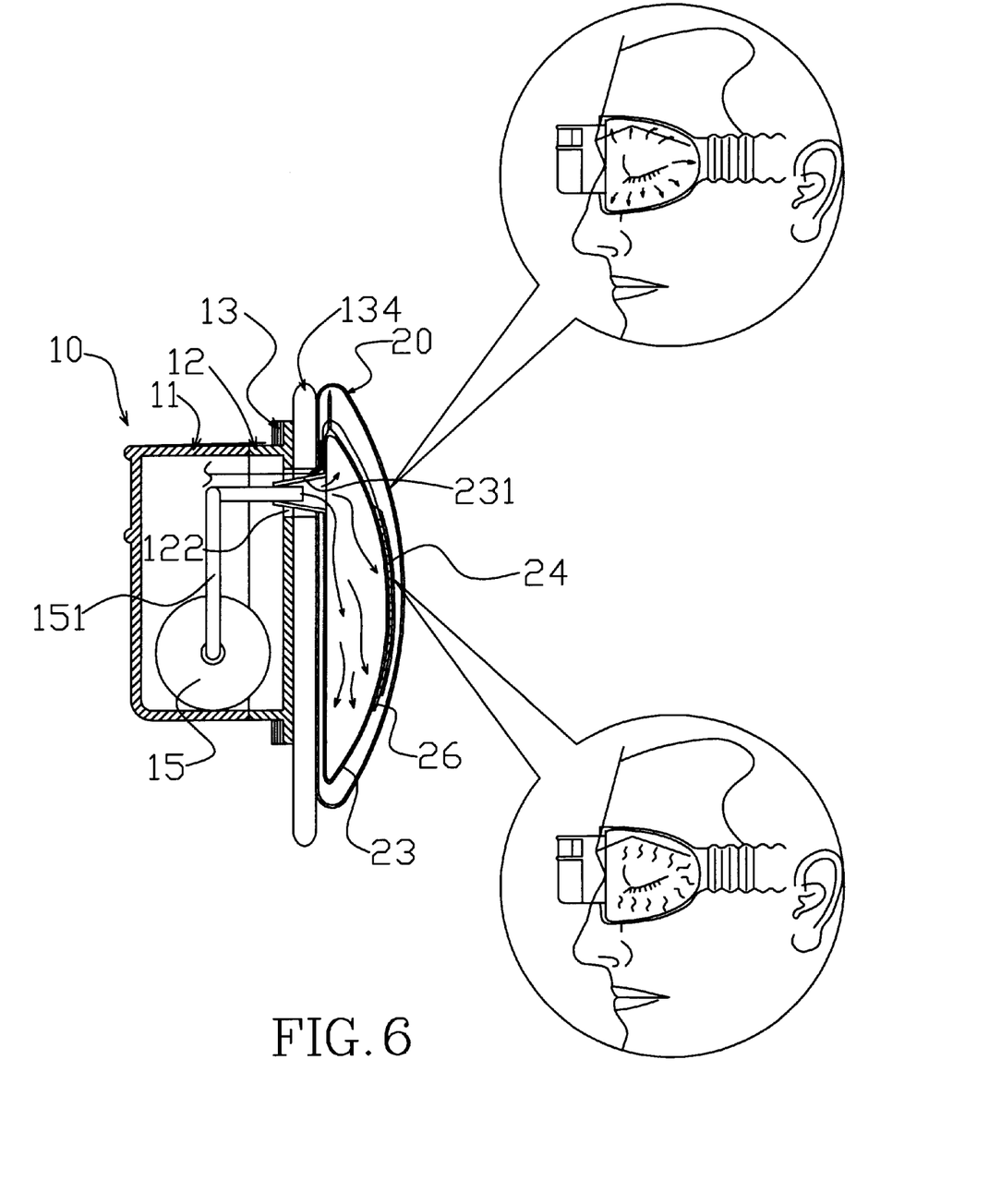
FIG. 6 is a schematic view illustrating the vibrating massage of the eye mask of the present invention.

Referring to FIG. 6, a pair of vibration motors 17 are mounted within the main body 10, corresponding to the eyes of the human body. The action of the vibration motor 17 is that the vibration action can evenly massage the surrounding of the eyes. The wearer can adjust the controller 30 so as to provide the most suitable massage action to the wearer.

Referring again to FIG. 2, at the mounting area of the two vibration motors 17, i.e., at the rear cover 12, a slot 123 is provided to avoid the vibration force being eliminated by the rear cover 12, but to concentrate at the mounting area in order to provide a strong vibration force to the eyes.

Figure 7:
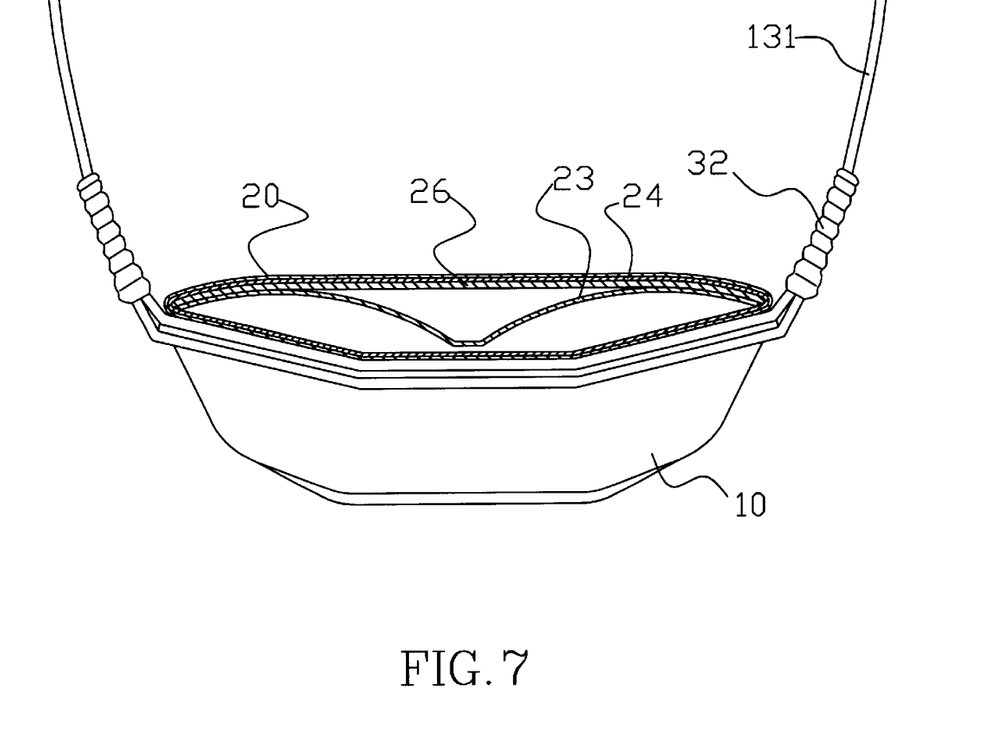
FIG. 7 is a schematic view illustrating the heat insulation liner of the eye mask of the present invention.

Referring to FIG. 7, the air sac 23 is designed into an expanded shape. The heat emitting element 24 is adhered to the heat insulation liner 26 in order to avoid deformation of the air sac 23.

Referring to FIGS. 7 and 8, the elastic tightening strap 131 can be elastically mounted onto the head of the human body. After the air sac 23 is expanded during massaging, the air sac 23 will deflated and the belt 131 will cause the eye mask to press against the eyes. In order to avoid this, the main body 10 is made from a hard material and a pivot is provided to the left, right side, and the middle section of the main body 10. Thus, a tolerance is provided to the air sac 23 and the eyes. Thus, the pressure of the air sac 23 will not be affected, and the air sac 23 after it is flattened will not press against the eyes.

There have been shown and described a multifunctional eye mask. Many modifications, changes, variations and other applications of the subject matter will become apparent to those skilled in the art. However, all these modifications changes and variation which do not depart from the spirit and scope of the invention are deemed to be covered by the invention which is limited by the claims.

What is claimed is:

1. A structure of a multifunctional eye mask comprising an elastic tightening strap, a main body, a heat healing device and a controller, wherein the elastic tightening strap is used to tie the mask to the eyes of user, a section of the strap is mounted with the main body and the heat healing device, and the main body includes an air pump, an air releasing valve, a tube, a pair of vibration motors, a buzzer, a wiring board, and the exterior of the main body is provided with wires linked to the controller, the heat healing device consists of a front and a rear protective plates formed into a mask structure containing an air sac, a heat-emitting element, an air inlet for the air sac and the heat-emitting element are connected to the main body, the controller is provided with a circuit device with controlling switches and adjusting knobs on the surface of the controller, thereby when in use, by means of the circuit device, the air sac expands and contracts and the heat emitting element emits heats, and the air sac and the heat emitting element are preset in the controller such that the eyes are provided with an intermittent massage, heat healing treatment and vibrating massage.

2. A structure of a multifunctional eye mask as set forth in claim 1, wherein the elastic tightening strap is provided with an retractable section, and a fastener at both ends of the strap, and the tightening strap is provided with a fixing plate, wherein the main body consists of a front cover, a protruded edge provided to front and rear covers to mount with the fixing plate such that the surface of the rear plate is mounted at the back of the fixing plate.

3. A structure of a multifunctional eye mask as set forth in claim 1, wherein the heat emitting element is located at an heat insulation liner by an adhesive plate, and the lateral sides of the heat insulation liner is mounted to the front and rear protective plate.

4. A structure of a multifunctional eye mask as set forth in claim 1, wherein an external edge and surface of the rear protective plate adjacent to the eyes is provided with a plurality of infra red protrusions and magnetic stones.

5. A structure of a multifunctional eye mask as set forth in claim 1, wherein a liner is provided in between the main body and the heat healing device, and the lateral sides of the liner and the retractable section of the tightening strap are connected.

6. A improved structure of a multifunctional eye mask as set forth in claim 1, wherein the pair of vibration motors are adapted to provide vibration massage to the eyes, and the rear cover of the main body is provided with a slot so that the vibration is concentrated to the eyes.

* * * * *